United States Patent [19]

Tournier et al.

[11] Patent Number: 5,587,199
[45] Date of Patent: Dec. 24, 1996

[54] PROCESS OF PREPARING PARTICLES FOR NMR IMAGING

[75] Inventors: Hervé Tournier, Valleiry; Roland Hyacinthe, Douvaine, both of France; Michel Schneider, Troinex, Switzerland

[73] Assignee: Bracco International B.V., Switzerland

[21] Appl. No.: 421,329

[22] Filed: Apr. 13, 1995

Related U.S. Application Data

[62] Division of Ser. No. 96,414, Jul. 26, 1993, Pat. No. 5,464,696.

[30] Foreign Application Priority Data

Aug. 13, 1992 [EP] European Pat. Off. ............. 92810618
May 25, 1993 [EP] European Pat. Off. ............. 93810380

[51] Int. Cl.$^6$ ............. B05D 7/00; B05D 3/12; B32B 9/00; B06B 1/00
[52] U.S. Cl. ............. 427/2.12; 427/2.14; 427/220; 427/600
[58] Field of Search ............. 427/2.12, 2.14, 427/600, 220; 424/9; 128/653.4

[56] References Cited

U.S. PATENT DOCUMENTS

| | | | |
|---|---|---|---|
| 4,331,654 | 5/1982 | Morris | 424/38 |
| 4,675,173 | 6/1987 | Widder | 424/9 |
| 4,728,575 | 3/1988 | Gamble et al. | 428/402.2 |
| 4,863,715 | 9/1989 | Jacobsen et al. | 424/9 |
| 4,929,589 | 5/1990 | Martin et al. | 427/220 |
| 4,983,566 | 1/1991 | Wieserman et al. | 427/220 |
| 4,994,429 | 2/1991 | Wieserman et al. | 427/220 |
| 5,091,188 | 2/1992 | Haynes | 424/450 |
| 5,124,289 | 6/1992 | Martin et al. | 427/220 |
| 5,160,725 | 11/1992 | Pilgrimm | 424/9 |
| 5,230,882 | 7/1993 | Unger | 424/9 |
| 5,246,707 | 9/1993 | Haynes | 424/450 |
| 5,405,766 | 4/1995 | Kallury et al. | 435/174 |
| 5,411,730 | 5/1995 | Kirpotin et al. | 424/322 |
| 5,494,744 | 2/1996 | Evenhart et al. | 427/600 |

FOREIGN PATENT DOCUMENTS

| | | |
|---|---|---|
| 0220797 | 5/1987 | European Pat. Off. . |
| 0249229 | 12/1987 | European Pat. Off. . |
| 0272091 | 6/1988 | European Pat. Off. . |
| 0284549 | 9/1988 | European Pat. Off. . |
| 0354855 | 2/1990 | European Pat. Off. . |
| 0467275A1 | 1/1992 | European Pat. Off. . |
| 0494615A1 | 7/1992 | European Pat. Off. . |
| 8414761 | 4/1985 | France . |
| WO91/14454 | 10/1991 | WIPO . |

OTHER PUBLICATIONS

R. H. Muller et al. "In Vitro characterization of . . . " Journal of Controlled Release 20 (1992) Aug., No. 3, Amsterdam NL, pp. 237–246.

Database WPIL Week 9241, Derwent Publication Ltd., London, GB, AN 92-337723 & JP-A-4 244 017 (Kyowa Hakko Kogyo) 1. Abstract. (no date available).

*Primary Examiner*—Diana Dudash
*Attorney, Agent, or Firm*—Nixon & Vanderhye

[57] ABSTRACT

Magnetite particles suitable for injection into the blood stream of patients having enhanced resistance against agglomeration and uptake by the RES of the liver and spleen. The particles essentially consist of an iron oxide core and a phosphoric acid mono alkyl or alkenyl ester or glycerophospholipid/surfactant three dimensional shell surrounding the core. The core and the monoester or a micellar glycerophospholipid form an urchin-like structure which is further interlaced or intertwined with a non-ionic surfactant to produce a protective three dimensional shell which renders particles almost undetectable by the macrophages. Particles prepared according to the invention are kept in the blood circulation for long periods and represent excellent long lasting blood pool agents. Key components in the shell are (a) a polybasic mineral-organic species such as glycero phosphatidic acid in micellar form and (b) a block copolymer having successive hydrophilic and hydrophobic segments.

8 Claims, 2 Drawing Sheets

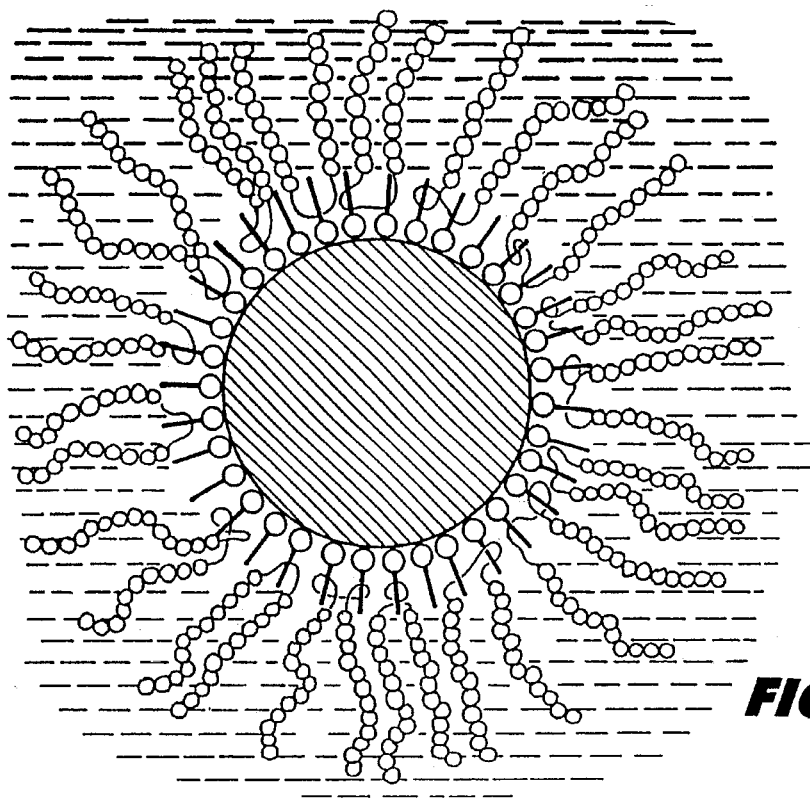
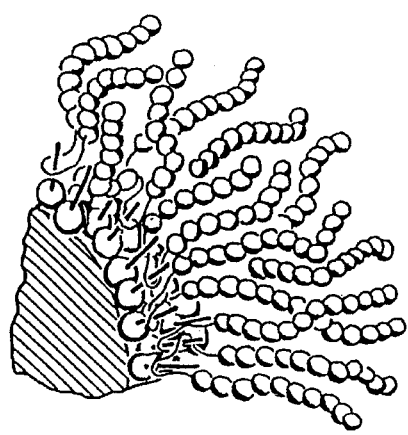
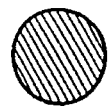
FIG. 1C
FIG. 1D
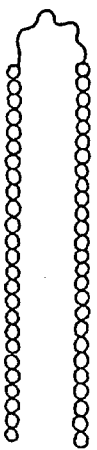
FIG. 1B
FIG. 1E

PROCESS OF PREPARING PARTICLES FOR NMR IMAGING

This is a division of application Ser. No. 08/096,414, filed Jul. 26, 1993 now U.S. Pat. No. 5,464,696.

FIELD OF INVENTION

The invention relates to iron oxide particles which when in suspension are injectable into the blood stream of patients. The particles have enhanced stability against agglomeration, and being relatively "invisible" to the reticulo-endothelial system (RES), they show an increased resistance to removal by macrophages. The particles are useful for production of contrast agents for blood-pool imaging.

BACKGROUND ART

Use of iron oxide particles in the form of injectable aqueous suspensions for diagnostic purposes has attracted much interest in the past. Ferromagnetic species or superparamagnetic magnetite microcrystals have been used as contrast agents for the nuclear magnetic resonance imaging (MRI) of the liver and spleen. Their use as contrast agents in these organs is based on the observation that soon after injection the particles are recognized by the RES and rapidly captured. The particles are then removed from the bloodstream, stored in the liver and spleen and subsequently eliminated. Much effort has been devoted toward improvement of the known formulations with the aim to increasing the uptake of the superparamagnetic particles in the targeted organs e.g. liver, spleen or bone marrow prior to their elimination from the body thus rendering their use more practical.

With the development of NMR analysis, it has been recognized that a considerable improvement of the technique and an important advance in the art would be achieved by providing a contrast agent whose properties would enable use of NMR analysis on the entire body and not only on certain of its parts. For this purpose, however, it would be necessary to produce a medium whose magnetic properties are at least as good as those of the iron oxide particles known to date but having a residence time in the blood stream which outlasts any other particle known in the art. Hence, in this regard the problem to be solved was to find a particle which for a given period of time would not be recognized by the RES. Yet, it has been reported that improved iron oxide particles may be obtained through the use of various coating materials which when applied thereto, either modify residence times or assist the delivery of the particles to other specific sites in the animal or human body.

EP-A-0 272 091 (VESTAR) discloses coating solid particles of an active ingredient, i.e. magnetite (and other diagnostic agents or drugs) said ingredient constituting the core of the particles, with a first layer of a monomolecular amphiphile which can associate with the ingredient of the core; then, the system comprises a second outer layer, which may include a bimolecular layer of phospholipids (i.e. a liposome membrane analog) which encapsulates the amphiphile. In the examples magnetite particles coated with palmitic acid as surfactant were encapsulated in liposomes made from a mixture of cholesterol and distearoylphosphatidylcholine. One object of the arrangement is to stabilize the active ingredient in the circulation against removal.

EP-A-0 275 285 (ADVANCED MAGNETICS) discloses coated and uncoated magnetite particles for use as a contrast agent for NMR imaging. When coated, the particles are surrounded by a polymer to which biologically active molecules may be attached. In the case of coated particles, the biological molecules can be chosen to target specific organs or tissues. Polymeric coatings disclosed may be made from proteins such as albumin, polysaccharides such as dextran, polypeptides such as polyglutamates or polylysines or organosilanes such as N-2-aminoethyl-3-aminopropyltrimethoxy-silane. Biological molecules that may be covalently attached to the coating are antibodies, carbohydrates or hormones which may enhance specificity and biodistribution of the particles to specific sites in the organism.

EP-A-0 354 855 (TERUMO) discloses liposomes as drug-carrier vesicles containing polyethylene glycol bound phospholipid in the lipid layer of the vesicle. The hydrophobic moiety of the phospholipid is sunk in the membrane-constituting lipids or is bound thereto, while the hydrophilic moiety of the polyethylene glycol protrudes therefrom and extends into the surrounding medium. The liposomic vesicles are said to be useful for preparation of artificial erythrocytes by encapsulation of hemoglobin in the vesicles.

U.S. Pat. No. 4,904,479 (ILLUM) discloses coating polystyrene particles with amphiphilic block copolymers having simultaneously hydrophilic and hydrophobic segments (e.g. Poloxamer® and Poloxamine®). The coating is intended to minimize opsonization after injection and enable directing the particles to the bone marrow rather than to the liver or spleen. Poloxamer® and Poloxamine® are amphiphilic block copolymers comprising consecutive hydrophobic polyoxypropylene segments and hydrophilic polyoxyethylene segments; it is believed that for protection against uptake by the liver, the hydrophilic segments stick out from the surface of the particle outer coating, thus sterically preventing the deposition thereto of opsonin and making the particles less recognizable by the macrophages.

Although the methods of the prior art have merit, they deal with only a very specific problem of particles which can be selectively targeted to different but specific sites (e.g. liver, spleen, lungs, lymph nodes, bone marrow, etc.) whereas the present invention is set out to solve a problem of production of particles which will not be recognized by the RES, which will remain in the blood for prolonged periods of time and which would be useful for production of long lasting blood pool agents.

The particles of the prior art require expensive manufacturing techniques and produce particles which, upon injection, are recognized by the RES and easily removed from the blood. Such particles and the contrast agents produced therefrom cannot be used in applications for which a relatively long biological half-life is required.

Contrast agents with prolonged presence in the blood i.e. good resistance to uptake by RES and a relatively low diffusivity into the tissue or extravascular spots are recognized in the art as particularly useful "blood pool" agents. Long biological half-lifes are sometimes desirable for the blood pool agents if one wants to produce meaningful analytical results eliminating repeated injections and heavy use of contrast media. For obtaining such long lived blood pool agents, it would be necessary to produce "stealth" particles which, for a period of time, would not be recognized by the RES and which would still provide sufficient magnetic relaxation response. Existence of a real "stealth" iron oxide particle would enable NMR analysis of the body as a whole and not only analysis of localized parts or specific organs, as done with contrast agents known so far. The stealth particles would thus make possible measurements of blood volumes and the blood perfusion of various organs, including brain, using non-invasive techniques. For instance, monitoring variations in blood oxygenation of the brain cortex during activation tasks would become possible.

Also, particles which could remain in the blood stream for long periods would provide very valuable information on the cell status and distribution of nutrients in various organs under different physical conditions. The contrast agents made with such particles would enable direct insight into blood microcirculation and metabolic cycles of cells in the body and would therefore, open new avenues to better understanding of processes in living organisms leading to better detection of anomalies such as growth of tumors. However, the prior art has not yet succeded in providing a long lasting magnetite particles and, therefrom, blood pool contrast agents which would enable these analytical techniques to perform such measurements and to produce the desired data.

SUMMARY OF THE INVENTION

Briefly summarized, the invention relates to blood pool contrast agents for diagnostic image analysis of human or animal body, preferably by MRI analysis, which remain in the blood stream for prolonged periods of time and thus enable measurements of blood volumes and the blood perfusion of various organs. More specifically, the invention relates to contrast agents which are particularly resistant to rapid uptake by the RES and which, upon injection, remain present in the blood stream much longer then the blood pool contrast agents known so far. The blood pool agents of the invention comprise iron oxide particles stabilized by a three dimensional shell layer containing molecules of an amphipatic compound and a non-ionic surfactant. The amphipatic compound has a hydrophilic negatively charged phosphorus containing head moiety bonded to a hydrophobic tail moiety and is characterized by being in micellar form. The non-ionic surfactant of the three dimensional shell layer causes the amphipatic compound to be in said micellar form and the hydrophilic phosphorus containing (preferably phosphoryl) head moiety of the amphiphile bears at least two negative charges. The three dimensional shell is formed from molecules of the amphipatic compound whose negative phosphoryl head moieties are pointing towards the iron oxide core and the hydrophobic tail moieties protrude outwardly therefrom forming an urchin-like structure. The urchin-like structure serves as a base for building the three dimensional shell by anchoring thereto the non-ionic surfactant. When the amphipatic compound is a mono alkyl or alkenyl phosphoric acid ester or glycerophospholipid, the outer layer comprises a non-ionic surfactant whose hydrophobic moieties are interlaced or intertwined with the alkyl or alkenyl chain of the ester or glycerophospholipid further stabilizing the structure. In either case, the natural ability of the non-ionic surfactant to cause micellization of these compounds is to be deployed.

The preferred glycerophospholipids consist of a monophosphate ester of a substituted or partially substituted polyalcohol, at least one other alcoholic function of said polyalcohol being esterified by a long chain, saturated or unsaturated, aliphatic fatty acid, or etherified by a long chain, saturated or unsaturated alcohol, the other two acidic functions of the phosphoric acid being either free or salified with alkali or earth-alkali metals. More specifically, the glycerophospholipid is preferably a monophosphate of a fatty acid glyceride selected from dimyristoylphosphatidic acid, dipalmitoylphosphatidic acid, or distearoylphosphatidic acid.

A preferred non-ionic surfactant is a physiologically acceptable surfactant with at least one block-copolymer having polyoxyethylene and polyoxypropylene segments or polyethyleneglycolhexadecylether. Surfactants of this kind are commercially available under the trademarks of Pluronic®, Poloxamer®, Poloxamine®, Synperonic® or BRIJ®.

After preparation, the particles of the invention may be sterilized and then lyophilized to produce a sterile powder which can be stored for prolonged periods. In such case the contrast agent of the invention is reconstituted from the lyophilized pulverulent formulation by dispersing the powder in a physiologically acceptable liquid carrier. The suspension obtained is ready for administration.

The invention further relates to a process of manufacturing of particles as well as their use as contrast agents in NMR imaging of human or animal body.

BRIEF DESCRIPTION OF THE DRAWINGS

FIG. 1A is a cross-sectional schematic diagram of an iron oxide urchin-like structure pertaining to the particle of the invention with non-ionic surfactant forming a three dimensional shell around the particle.

FIG. 1B is a section of a three-dimensional view of the iron oxide urchin-like structure pertaining to the particle of the invention.

FIG. 1C is a representation of a magnetite particle forming the core of the particle of the invention;

FIG. 1D is a representation of a glycerophospholipid or monoester of phosphoric acid;

FIG. 1E is a representation of the surfactant showing anchoring via its hydrophobic polyoxypropylene segments.

DETAILED DESCRIPTION OF THE INVENTION

Figure 2:
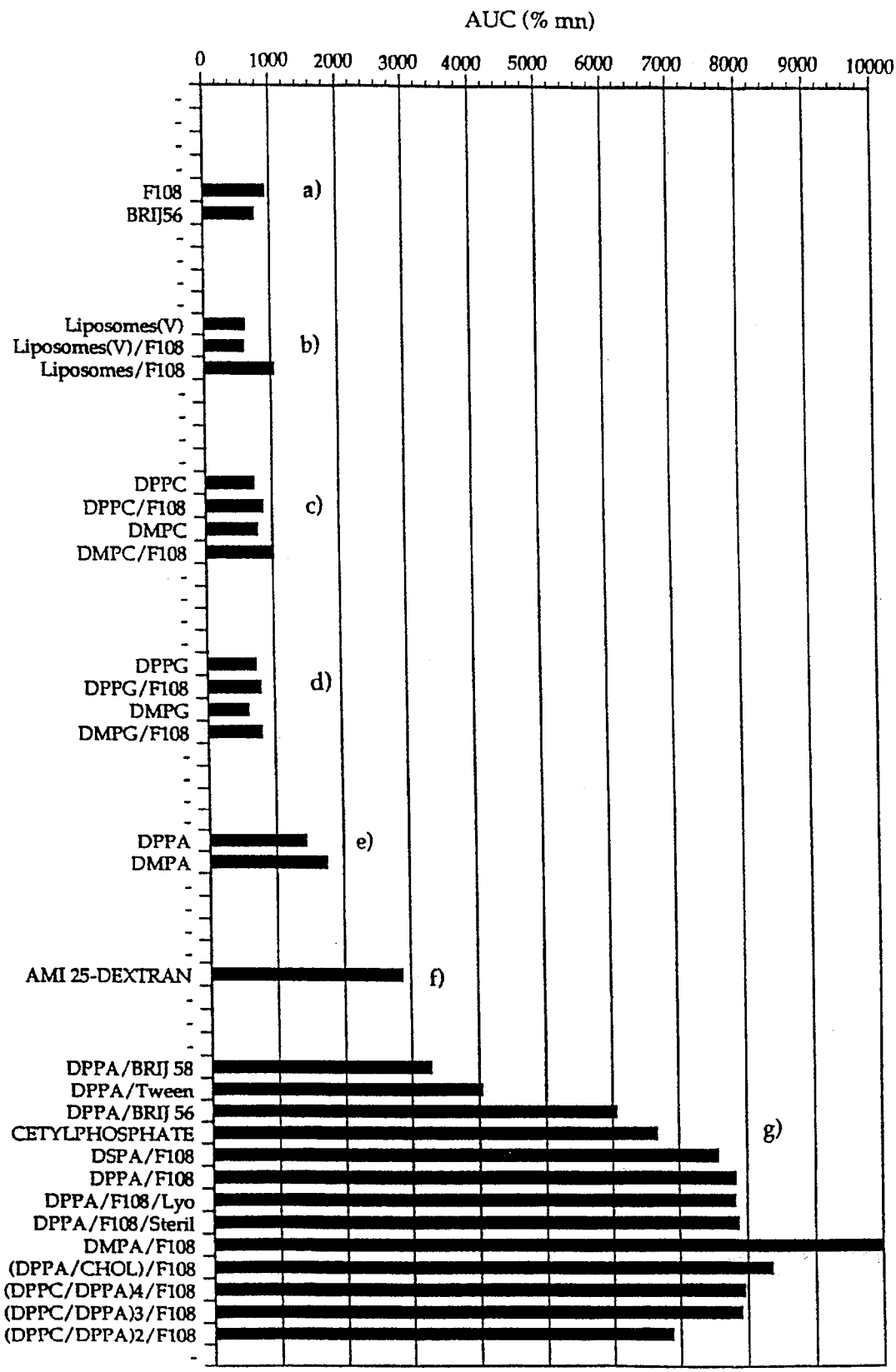
FIG. 2 is a schematic diagram showing comparison of residence times or "activity" (expressed as the Area Under Curve (AUC) of iron oxide particles of the invention and that obtained for particles of the prior art.

The particles of the present invention comprise an iron oxide core and an outer layer consisting of molecules of an amphipatic compound and a non-ionic surfactant. The amphipatic compound which has a relatively strongly charged hydrophilic moiety that sticks to the surface of the iron oxide may be a mono alkyl or cycloalkyl or alkenyl phosphoric acid ester or a negatively charged phospholipid. The term "cyclo" used here implies that the cyclic part of the molecule may be 5–7 membered, may be saturated or not (aromatic) or may contain heteroatoms (heterocycles). In either case, the outer layer having the shape of a three dimensional shell comprises a non-ionic surfactant whose hydrophobic moieties are interlaced or intertwined with the alkyl or alkenyl chain of the ester further stabilizing the three dimensional structure. The non-ionic surfactant must also be able to micellize the phosphoric acid monoester or phospholipid as only when in micellar form, these compounds will exhibit sufficient affinity for the iron oxide core and, consequently may be used as stabilizers of magnetite particles. The affinity between the phosphoryl head and $Fe_3O_4$ must be such that, in the presence of a non-ionic surfactant and upon sonication, the micellar phospholipid or monoester form an urchin-like precursor which subsequently serves as template for the construction of the outer three dimensional shell which is built through the interaction of the hydrophobic segments of the surfactant and the hydrophobic moieties of the amphipatic compound. The three dimensional structure will then provide a stable "RES non-recognizable" particle. Hence, in the blood pool agent of the invention, it is important that the amphipatic compound, preferably a glycerophospholipid, forming the outer layer does not form liposome vesicles or a liposome-like film around the iron oxide core. This is so because the three dimensional shell is formed from phospholipid molecules whose negative phosphoryl head moieties point towards the iron oxide core and the hydrophobic tail moieties protrude outwardly therefrom forming the urchin-like precursor structure. The urchin-like structure always serves as foundation for building the three dimensional shell or layer, whether the starting amphipatic compound is a mono alkyl or mono alkenyl phosphoric acid ester or a micellar glycerophospholipid. In either case the resulting particles have increased stability against removal and will exhibit excellent contrast agent properties. It should be born in mind that amphiphilic molecules participating in liposome-like films are organized in a reverse order tail-to-tail, the hydrophilic heads prodruding outwardly.

When glycerophospholipids are used, for obtaining the urchin-like base around the iron oxide particles whereby the complete three dimensional shell can be constructed, it is important to either (a) energize the iron oxide particles in the presence of a glycerophospholipid and a non-ionic surfactant simultaneously or (b) prepare a suspension of the iron oxide particles with a glycerophospholipid, energize the suspension, add a non-ionic surfactant and then, optionally repeat the energizing step. Energizing is carried out by dispersing the iron oxide particles evenly or homogenizing the dispersion which accelerates micellization and/or destruction of liposomes or laminates which may have formed earlier. Energizing may be effected using various methods including agitation; however, sonication, microfluidization, advantageously under moderate heating (30°–50° C.) are preferred.

It is postulated, that the construction of the three dimensional shell which stabilizes the particles is carried out via an urchin-like basic structure formed between the iron oxide and the glycerophospholipid in micellar form. The phospholipids are first micellized by sonication or microfluidization in the presence of the surfactant and then the negative charges of the amphiphile in the micelles interact with the iron oxide core while their electrically neutral hydrophobic ends are attracted by the surfactant.

Experimental evidence indicates that during the process of formation of the three dimensional shell, the surfactant serves several functions. It causes micellization of the amphiphile, it assists orientation and structuring of the micelles around the core (facilitating formation of the urchin-like precursor) and finally anchors itself to the hydrophobic segments of the amphiphile to provide a three dimensional shell around the particle.

Clearly, formation of the intermediate urchin-like structure, such as that illustrated in FIGS. 1(a & b), is extremely important since it has been found that non-ionic surfactant alone cannot provide sufficient protection of magnetite particles against rapid uptake by the RES. It has been found that the use of phospholipids alone or in combination with non-ionic surfactants would not yield particles which are practically useful as long lived blood pool contrast media unless prepared according to the invention. Thus, successful stabilization of iron oxide particles against premature removal from the blood stream may be achieved through the use of phospholipids, only if the phospholipid liposomal structure, which normally exists around particles in the formulations of prior art, is destroyed. This has been found to be so even with magnetite suspensions which, in addition to phospholipids, contain polyoxyethylene (POE)/polyoxypropylene (POP) surfactants. Therefore, the block-copolymer surfactant will operate as desired only if it is properly stabilized in the outer position of the shell around the magnetite core. Its simple presence in the suspension is not sufficient. This is so even if the same suspension contains phospholipid stabilized magnetite i.e. if magnetite particles are first coated with phospholipid (which then spreads as a laminar film on the $Fe_3O_4$ surface) and the surfactant is added afterwards with no energization. The above conclusion is supported by the observation that only a three dimensional, e.g. urchin-like structure formed with micellar phospholipids is capable of capturing and anchoring enough surfactant to provide a stable RES stealth iron oxide particle.

Presumably, the anchoring of the surfactant FIG. 1E occurs via its hydrophobic polyoxypropylene (POP) segments which interact with the hydrophobic part of the glycerophospholipid or a monoester of phosphoric acid FIG. 1D. As suggested in FIGS. 1A and 1B the hydrophobic part is anchored by Van der Waals forces with the polyoxypropylene (POP) segments while the hydrophilic polyoxyethylene (POE) segments protrude outwardly into the solution, thus probably inhibiting opsonisation and agglomeration of the magnetite particles FIG. 1C.

In the case of alkyl or alkenyl esters of phosphoric acid, the formation of the urchin-like structure is basically the same as above and the non-ionic surfactant has its hydrophobic moieties interlaced or intertwined with the alkyl or alkenyl chains of the phosphoric acid ester and its hydrophilic moieties protrude into the solution.

The exact nature of the interactions between the iron oxide core and the phosphoryl head moieties is not exactly known. However, it has been found that for good resistance in blood of the "stealth" iron oxide particles of the invention, it is important that the negative charges of both oxygen atoms in the phosphoryl moiety stay available for interaction with the core. Thus, when only one negative oxygen site is available the particles produced do not have the same stability and are more easily removed from circulation. So far, the importance and stability of this interaction has not been recognized in the art and, therefore, this may explain why previous attempts to produce long lasting magnetite blood pool particles failed.

It has been found that when phospholipids in which the negative charges are neutralized, as for example in the case of dipalmitoylphosphatidylcholine (DPPC) or dimyristoylphosphatidyl choline (DMPC), are employed, the corresponding particulate structures formed are poorly protected and the contrast agents made with these compounds may be useful for imaging liver and spleen but not as long lasting blood pool agents, as such particles are not protected from premature removal from the blood stream. The same applies to phospholipids whose phosphoryl head moieties have only one negative charge available for interaction with the magnetite core. For example, dipalmitoylphosphatidylglycerol (DPPG), dimyristoylphosphatidyl glycerol (DMPG) or dicetylphosphate (DCP) are amphiphiles which will produce particulate structures that are inadequately protected against rapid removal from blood. The contrast agents made this way are, therefore, not useful as a blood pool agents as they will have a relatively short residence time in the blood stream. On the other hand, when phospholipids whose negative charges on both oxygen atoms in the phosphoryl moiety are available for interaction with the core are used, the resulting structures are extremely stable and the iron oxide particles produced with these compounds are well protected against removal from the blood stream. Examples of such compounds are dipalmitoylphosphatidic acid (DPPA) and dimyristoylphosphatidic acid (DMPA).

To ensure good stealth properties of the particle the compound immediately adjacent to the particle should have, in addition to the availability of the negative charges on both oxygen atoms in the phosphoryl head, a relatively long alkyl or alkenyl chain or a hydrophobic cycloalkyl attached to the phosphorus atom, either directly, or via an intermediate alkylene or oxygen bridge. Therefore, to obtain the stable stealth particles and therefrom the contrast agents of the invention, the compound immediately adjacent to the magnetite core must be a mono alkyl or alkenyl or cycloalkyl containing ester of phosphoric acid, a monoalkyl phosphonate or a glycerophospholipid whose alkyl or alkenyl chains have a relatively strong hydrophobic character. Experiments have shown that only alkyl or alkenyl chains of sufficient length can properly interact with another amphipatic compound, and provide an anchor for a sufficient mount of the non-ionic surfactant or block copolymer to produce a stable three dimensional structure around the iron core. Alkyl or alkenyl chains with at least eight carbon atoms, preferably with at least ten and more preferably at least twelve carbon atoms are particularly desirable. Short hydrophobic alkyl or alkenyl chains or macrocycle ligands do not provide stable particles which indicate that one should have either a firm interaction between the intermediate layer and the surfactant, or sufficient amount of anchored surfactant must be available to obtain the desired result. Lack of appreciation of this feature may be another possible explanation as to why RES invisible or stealth iron oxide particles have not, until now, been available as practically useful long lasting blood pool agent. Among the monophosphate esters suitable in the present invention, one may cite $C_8$–$C_{18}$ alkyl and alkenyl phosphates, cholesteryl-phosphate, cyclohexyl-decyl-phosphate, cetylphosphate, cumyl phosphate, and the like.

Thus according to the invention, a very efficient protection of the particles against removal from circulation may be obtained if a primary layer immediately adjacent to the particle comprises an amphipatic substance with a relatively strongly ionized negative function and a relatively long and efficient hydrophobic organic chairs, and that a further layer interlaced or intertwined therewith is built from a block copolymer having, in succession, hydrophilic and hydrophobic segments, e.g. surfactants of the Poloxamer®, Synperonic® or Pluronic® type. The effect of the substances of the primary layer defined as mono alkyl or alkenyl phosphoric acid ester or phosphonate was totally unexpected and dumbfounding, particularly in view of some prior art (see WO 91/09629 page 17, first paragraph) which indicates that the presence of negatively charged phospholipids in the membrane of liposomes will increase the uptake of said liposomes by the reticulo-endothelial system.

It has also been found that for the particles of the invention, the quantities of mono alkyl phosphoric acid ester or glycerophospholipid and block copolymer, relative to each other, should be substantial, i.e. the weight ratio of the earlier to the later should be in the range from 1:100 to 10:1, preferably from 1:30 to 5:1 and more preferably from 1:10 to 1:1. Also, the weight ratio of the mono alkyl phosphoric acid ester to that of the iron oxide core should be between 1:5 and 100:1 preferably between 20:1 and 1:1. Some experimental data also suggest that the ratio of the surfactant to the micellar phospholipid or the monoester of phosphoric acid should be kept within certain limits, as too much of the surfactant may disperse the phospholipid or the monoester so much that the affinity thereof for the magnetite particle is diminished and the formation of the urchin-like structure impeded. By the same token, particles prepared with too little of the surfactant will agglomerate and will not be sufficiently protected from opsonization.

It has been established that the stable, to the RES invisible, particles may be produced from a mixture of two or more compounds selected from ionic and neutral phospholipids, mono alkyl or alkenyl esters of phospholipids and/or other non-phospholipid compounds by a method in which iron oxide particles are suspended or admixed with a negatively charged amphipatic compound or a mixture of the negatively charged phospholipids and other non-phospholipids and a surfactant, in a physiologically acceptable aqueous phase. The mixture formed is sonicated or microfluidized to micellize the amphipatic compound, create an urchin-like structure and, therefrom, a three dimensional shell around the iron oxide particles. The particles obtained are well protected from premature removal from circulation and are found to be very useful as excellent blood pool imaging agents. Examples of non-phospholipid compounds which may be useful for the stable magnetite particles of the invention are compounds like cholesterol, ergosterol, phytosterol, sitosterol, lanosterol, tocopherol, etc..

After the sonication or microfluidization, the mixture may be further sterilized and/or lyophilized to produce a dry powder with a long shelf life.

In a variant of the method, the surfactant may be added to the mixture of the iron oxide and the amphipatic compound after the sonication or microfluidization. In such a case, however, the sonication, microfluidization or heating step is optionally repeated with all the components together.

The suspensions of the invention may also be prepared from pulverulent or powder formulations comprising iron oxide particles. Formulations in powder form are usually prepared by lyophilization or drying freshly prepared solutions comprising iron oxide particles, phospholipids and non-ionic surfactants. Prior to lyophilization or drying these solutions are sterilized. The sterilization may be carried out using any of the known techniques i.e. heating, filtration, γ-rays, etc. Alternatively, it may also be possible to sterilize suspensions obtained using lyophilized powders which were stored for a longer period of time.

Particles prepared according to the invention are found to be useful as blood pool contrast agents for in vivo NMR imaging of organs of human or animal body. The imaging is carried out by administering to patients, usually via an intravenous injection, an aqueous suspension of magnetite particles according to the invention in a physiologically acceptable aqueous carrier and analyzing the change of magnetic relaxation ($T_1$ & $T_2$ components) of the proton spin of $H_2O$ in the vicinity of organs under investigation in the magnetic field generated by an NMR analyzer.

The following Examples further illustrate the invention:

EXAMPLE 1

In 40 ml of water, there were dissolved 81.1 mg (0.3 mmol) of $FeCl_3 \cdot 6H_2O$ and 25.8 mg (0.13 mmol) of $FeCl_2 \cdot 4H_2O$ (total Fe=0.43 mmol or 24.01 mg). To this were added 0.1 mCi of $^{59}Fe$ (tracer quantity) in the form of $FeCl_3$. The mixture was stirred and an aqueous 7.5% solution of ammonia was added dropwise until the pH reached a stable value of 8.6. A suspension of black particles formed which was heated for 5 min at 75° C. and the particles were allowed to precipitate and settle at room temperature. The precipitate was washed three times by decantation with portions of 100 ml of water. After washing the particles were again suspended in 45 ml of water under agitation. The iron concentration in the suspension was 0.533 mg/ml.

To 10 ml of this suspension (5.33 mg of Fe) were added (as component (a)) 100 mg of the monosodium salt of dipalmitoylphosphatidic acid (DPPA Na) and sonication was effected for 20 min (BRANSON 250 Sonifier, 1/8" microprobe, output 20 (15–20 W). The temperature which rose to about 68° C. during sonication was allowed to drop to room temperature, and (as component (b)) 100 mg of Synperonic® F-108 (from ICI) or of Poloxamer®-338 were added. Sonication was then resumed for 15 min under the same conditions to ensure complete dispersion and destruction of the liposome vesicles and provide micellar phospholipid layer around the iron oxide particles.

The suspension of particles obtained according to the invention (Sample 1A) contained, per ml, 0.5 mg of iron, 10 mg of DPPA and 10 mg of the Synperonic® surfactant (weight ratio of (a) to (b)=1:1). Measurements by means of a COULTER Nanosizer counter apparatus indicated that the average particle size was 120 nm, with a polydispersity index of 3.

Other samples were made under similar conditions but replacing part of the DPPA by DPPC; this gave the following samples (mole ratio DPPC/DPPA): 1C (9:1); 1D (7.5/2.5); 1E (5:5); 1F (2.5/7.5). Finally, a control sample (1B) was made containing only DPPC.

DPPA are cleared much more slowly, the effect being variable to the amount of the negatively charged phospholipid. This effect becomes particularly significant for practical uses when the mole or weight ratio of DPPA to

TABLE 1A

| Min | $1D_2$ (7.5:2.5) | $1E_2$ (5:5) | $1F_2$ (2.5:7.5) |
|---|---|---|---|
| 10 | 23.3 | 26.9 | 24.4 |
| 30 | 10.3 | 8.9 | 7.2 |
| 60 | 6.6 | 4.3 | 3.0 |
| 90 | 4.9 | 2.8 | 1.8 |
| 120 | 3.8 | 2.0 | 1.4 |
| AUC % min | 1509 | 1369 | 1211 | total phospholipids is 1 to 4 or more. From the results in the Table, it can be also seen that for best protecting the particles against removal from circulation, the mount by weight of DPPA relative to the core is 5:1 or more.

If, in the foregoing experiments, the DPPA in the form of its monosodium salt is replaced by the free acid or by other water soluble salts (from other metals) similar results are obtained. Moreover, if the DPPA is replaced by other phosphatidic acids, such as the distearoyl-, dimyristoyl-, dilauroyl- analogs as well as the higher homologs ($C_{20-26}$ acids), the results are not significantly different. It should also be noted that in the absence of component (b), there is still obtained a degree of protection of the magnetite particles with component (a) alone. This, however, is insufficient for protecting particles to be used for diagnostic purposes. As shown by the results of Table 1A below for Samples $1D_2$,

TABLE 1

| | Sample | | | | | | | |
|---|---|---|---|---|---|---|---|---|
| Time (min) | 1A *0:10 | 1B *10:0 | 1C *9:1 | 1D *7.5:2.5 | 1E *5:5 | 1F *2.5:7.5 | $1V_1$ | $1V_2$ |
| 10 | 80.5 | 12.3 | 52.7 | 72.5 | 76.1 | 79.9 | 1.2 | 1.5 |
| 30 | 72.7 | 1.4 | 22.2 | 63.8 | 72.4 | 72.8 | 0.8 | 0.7 |
| 60 | 59.3 | 1.0 | 10.3 | 53.4 | 63.5 | 66.1 | 0.8 | 0.7 |
| 90 | 54.0 | — | 5.7 | 48.7 | 58.3 | 57.3 | — | — |
| 120 | 41.4 | — | 4.0 | 41.3 | 52.2 | 48.0 | — | — |
| AUC % min | 7545 | 747 | 2386 | 6865 | 7889 | 7941 | 562 | 561 |

* = DPPC/DPPA mole ratio

Further control samples were made using the teaching of the prior art document EP-A-0 272 091. By duplicating the procedure in Example 1 of this document Sample $1V_1$ was made. Magnetite particles were first coated with a monomolecular quantity of palmitic acid and then encapsulated in a lipid film made from a 2:1 mixture of distearoylphosphatidylcholine and cholesterol (DSPC/CHOL). Sample $1V_2$ was the result of further protecting $1V_1$ by a layer of Synperonic® F-108.

The various suspension samples were tested by injecting 1 ml aliquots into the caudal vein of laboratory Sprague-Dawley rats and, thereafter, removing blood samples at intervals of time indicated; then the blood samples were analyzed by γ-counting for the remaining iron and the results recorded in terms of % of original iron injected (ID) as a function of time. Characterization of the persistence of a given preparation in blood was carried out by determining the Area Under the Curve (AUC) for the % ID vs. time curve between time 0 and 120 min after injection. These results are presented in Table 1.

The results show a rapid clearance of all samples lacking the DPPA (1B, $1V_1$, $IV_2$). In contrast, the samples containing $1E_2$ and $1F_2$, respectively identical with corresponding Samples 1D, 1E and 1F, except that the Synperonic® is omitted. These results given in Table 1A are presented as percentage of the original iron dose remaining after the different time periods expressed in minutes.

TABLE 2

| | Sample | | |
|---|---|---|---|
| Time (min) | 1G | 1H | 1J |
| 0 | 100 | 100 | 100 |
| 5 | 15.6 | 16.5 | 15.1 |
| 10 | 3.1 | 3.4 | — |
| 15 | 0.8 | 1.5 | 8.3 |
| 30 | 0.4 | 0.8 | 3.6 |
| 45 | — | — | 2.9 |
| 60 | — | — | — |
| AUC % min | 355 | 371 | 543 |

In Table 2, there are results (from experiments run identically to those reported in Table 1) which show that when the DPPA (component a) is replaced by an analog compound having but only one ionic function on the phosphate group, i.e. dipalmitoylphosphatidyl glycerol (DPPG) (Sample 1G) the layer obtained offers practically no protection. This being so even with addition of Synperonic® (Sample 1H). As a control (Sample 1J), there are also provided in Table 2 results obtained with a sample of dextran coated magnetite (AMI-25 prepared according to EP-A-0 274 285 of Advanced Magnetics, Inc.).

EXAMPLE 2

Illustrations of experiments carried out under the conditions described in Example 1 and presented in FIG. 2 and Table 3 provide further support for early observation of the phenomena reported in the discussion of results reported in Example 1. Representative samples for groups b), c), d) and f) were prepared according to teachings of EP-A-0 272 091 and EP-A-0 274 285 respectively while all other samples were prepared according to the method of the invention described in Example 1. Results clearly demonstrate that magnetite particles prepared with only non-ionic surfactant (Group a) will rest in the circulation for a short period of time. Use of DSPC/cholesterol liposome vesicles with or without non-ionic surfactant does not improve the characteristics of the blood pool agents (Group b). Various phospholipids are claimed to be useful material for production of stable iron oxide particles. In reality, however, if the phospholipids whose negative charges are neutralized as for example in, the case of dipalmitoylphosphatidylcholine (DPPC) or dimyristoylphosphatidylcholine (DMPC) (Group c) are employed the corresponding structures formed are poorly protected and the contrast agents made may be useful for imaging of liver and spleen or the bone marrow but not as long lasting blood pool agents. Much the same has been found for phospholipids whose phosphoryl head moieties have only one negative charge available for interaction with the magnetite core. For example. dipalmitoylphosphatidylglycerol (DPPG), dimyristoylphosphatidylglycerol (DMPG) or dicetylphosphate (DCP) are phospholipids which will produce structures that are inadequately protected from fast removal from blood (Group d). It has further been established that even when phospholipids whose negative charges on both oxygen atoms in the phosphoryl moiety are available for interaction with the core are used in the absence of the non-ionic surfactant the resulting structures are not useful for long lived blood pool agents of the invention. This

TABLE 3

| Group | FORMULATIONS | AUC (% min) |
|---|---|---|
| a) | MAG/F 108 | 924 |
|  | MAG/BRIJ 56 | 763 |
| b) | MAG/LIPOSOMES/F 108 | 1039 |
|  | LIPOSOMES/MAG (V) | 610 |
|  | LIPOSOMES/MAG (V)/F 108 | 596 |
| c) | · MAG/DAPC | 1053 |
|  | MAG/DAPC/F 108 | 875 |
|  | MAG/DPPC | 725 |
|  | MAG/DPPC/F108 | 860 |
|  | MAG/DMPC | 774 |
|  | MAG/DMPC/F108 | 1011 |
| d) | MAG/DPPG | 728 |
|  | MAG/DPPG/F 108 | 791 |
|  | MAG/DMPG | 600 |
|  | MAG/DMPG/F 108 | 798 |
| e) | MAG/DPPA | 1428 |
|  | MAG/DMPA | 1736 |
| f) | AMI 25 (S)-DEXTRAN | 2866 |

TABLE 3-continued

| | | |
|---|---|---|
| g) | MAG/DMPA/F 108 | 9984 |
|  | MAG/DPPA/F 108 | 7813 |
|  | MAG/DPPA. 2 Na/F 108 | 7767 |
|  | MAG/DPPA/F 108 + STERILISATION | 7855 |
|  | MAG/DPPA/F 108 + LYOPHILISATION | 7804 |
|  | MAG/DSPA/F 108 | 7557 |
|  | MAG/SPA –3/F 108 | 7639 |
|  | MAG/CETYL PHOSPHATE/F108 | 6657 |
|  | MAG/(DPPC/DPPA):(7.5/2.5)$_2$/F 108 | 6865 |
|  | MAG/(DPPC/DPPA):(5.0/5.0)$_3$/F 108 | 7889 |
|  | MAG/(DPPC/DPPA):(2.5/7.5)$_4$/F 108 | 7941 |
|  | MAG/(DPPA/CHOL):(1/1)/F 108 | 8352 |
|  | MAG/DPPA/BRIJ 56 | 6051 |
|  | MAG/DPPA/TWEEN 80 | 4035 |
|  | MAG/DPPA/BRIJ 58 | 3278 |

Legend
Surfactants
Pluronic = Poloxamer 338 = Synperonic F 108 = Block copolymer with the copolymer sequence: (oxyethylene)$_n$ - (oxypropylene)$_m$ - (oxyethylene)$_n$
Phosphatidic acids
DLPA = 1,2-Dilauroyl-glycero-3-phosphatidic acid (saturated fatty acid $C_{12}$)
DMPA = 1,2-Dimyristoyl-glycero-3-phosphatidic acid (saturated fatty acid $C_{14}$)
DPPA = 1,2-Dipalmitoyl-glycero-3-phosphatidic acid (saturated fatty acid $C_{16}$)
DSPA = 1,2-Distearoyl-glycero-3-phosphatidic acid (saturated fatty acid $C_{18}$)
SPA-3 = 1,2-Dialkoyl-glycero-3-phosphatidic acid (obtained from soy, hydrogenated: mixture of fatty acids $C_{16}$ and $C_{18}$)
Phosphocholines (lecithines)
DMPC = 1,2-Dimyristoyl-glycero-3-phosphocholine
DPPC = 1,2-Dipalmitoyl-glycero-3-phosphocholine
DSPC = 1,2-Distearoyl-glycero-3-phosphocholine
DAPC = 1,2-Diarachidoyl-glycero-3-phosphocholine
P 90H = 1,2-dialkoyl-glycero-3-phosphocholine - Hydrogenated soy lecithin (mixture of fatty acids $C_{16}$ and $C_{18}$ = same as DPPC)
Phosphoglycerols
DMPG = 1,2-Dimyristoyl-glycero-3-phosphoglycerol
DPPG = 1,2-Dipalmitoyl-glycero-3-phosphoglycerol
Other
CHOL = Cholesterol
CETYL PHOSPHATE = Phosphoric acid mono ester of cetyl alcohol ($C_{16}$).
TWEEN = Polysorbate = Polyoxyethylene sorbitan fatty acid ester
BRIJ = Polyethyleneglycol hexadecylether
MAG(V) = Magnetite with liposomes prepared according to EP-A-0 272 091.
AMI 25 = Dextran-coated magnetite prepared according to EP-A-0 275 285.
DPPC/DPPA$_2$ = DPPC to DPPA weight ratio 7.5/2.5
DPPC/DPPA$_3$ = DPPC to DPPA weight ratio 5.0/5.0
DPPC/DPPA$_4$ = DPPC to DPPA weight ratio 2.5/7.5
Surfactants F 108
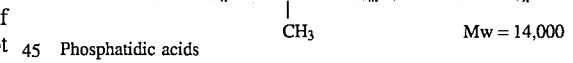
$$H-(O-CH_2-CH_2)_{\overline{n}}-(O-\underset{\underset{CH_3}{|}}{CH}-CH_2)_{\overline{m}}-(O-CH_2-CH_2)_{\overline{n}}-OH \qquad Mw = 14,000$$

Phosphatidic acids
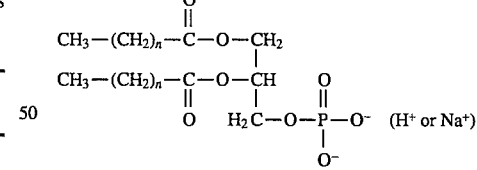
$$CH_3-(CH_2)_n-\overset{O}{\underset{||}{C}}-O-CH_2$$
$$CH_3-(CH_2)_n-\overset{O}{\underset{||}{C}}-O-CH \quad O$$
$$\qquad\qquad H_2C-O-\overset{||}{\underset{|}{P}}-O^- \quad (H^+ \text{ or } Na^+)$$
$$\qquad\qquad\qquad\qquad O^-$$

DLPA: n = 10
DMPA: n = 12
DPPA: n = 14
DSPA: n = 16

Phosphocholines
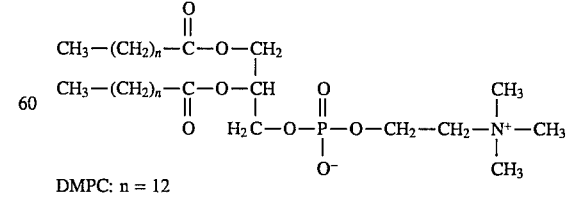
$$CH_3-(CH_2)_n-\overset{O}{\underset{||}{C}}-O-CH_2$$
$$CH_3-(CH_2)_n-\overset{O}{\underset{||}{C}}-O-CH \quad O \qquad\qquad CH_3$$
$$\qquad\qquad H_2C-O-\overset{||}{\underset{|}{P}}-O-CH_2-CH_2-\overset{|}{\underset{|}{N^+}}-CH_3$$
$$\qquad\qquad\qquad\qquad O^- \qquad\qquad CH_3$$

DMPC: n = 12
DPPC: n = 14
DSPC: n = 16

TABLE 3-continued

DAPC: n = 18
Phosphoglycerols

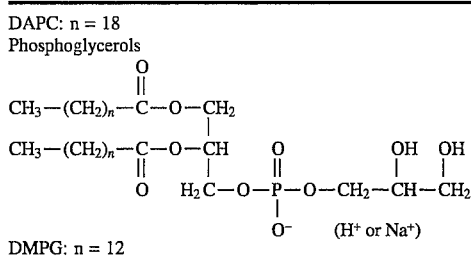

DMPG: n = 12
DPPG: n = 14 indicates that unless in micellar form even if dipalmitoylphosphatidic acid (DPPA) or dimyristoylphosphatidic acid (DMPA) are used the iron oxide particles produced will not be well protected against removal from the blood stream (Group e).

It was surprising to find, however, that protection of magnetite is better achieved using dextran than using the phospholipid formulations of the prior art (Group f). This was so even when these typically liposome formulations included non-ionic surfactants. Dextran coated magnetite particles are normally used as a contrast agent specifically designed for imaging the liver and spleen and are designed for relatively rapid removal from the blood stream.

When phospholipids whose negative charges on both oxygen atoms in the phosphoryl moiety are available for interaction with the core are used, the resulting magnetite particles are extremely stable in the blood circulation provided that the phospholipids are in micellar form. Thus iron oxide particles prepared with, for example, dipalmitoylphosphatidic acid (DPPA) in micellar form and Synperonic® F108 using the method of the invention will produce particles well protected against removal from the blood stream. The same applies when DPPA is replaced by DMPA, DSPA or cetyl phosphate or by mixtures of lecithines and phosphatidic acids (Group g). In analyzing the results, it has become apparent that the stability of the material in the blood stream may be rationalized using a model in which in the initial phase the phosphoryl head moieties of a phospholipid with a sufficiently long hydrophobic chain interacts with the magnetite core to form an urchin-like structure which then provides an anchoring layer for the non-ionic surfactant and thus constructs a three dimensional layer around the core. Also, different experiments have shown that use of non-ionic surfactants from different sources have only marginal influence on the end result.

The model proposed is further backed by the finding that phospholipid to non-ionic surfactant ratio although not very critical should be maintained between 0.01 and 10 preferably 0.1 and 1. As presented in Table 4, experiments have shown that for a constant concentration of iron oxide, magnetite particles produced with excess amounts of non-ionic surfactant (compared to that of DPPA) are not adequately protected from fast removal from blood. On the other hand,

TABLE 4

| $Fe_3O_4$ (mg/ml) | DPPA (mg/ml) | Synperonic F108 (mg/ml) | AUC (% min) |
|---|---|---|---|
| 0.5 | 0.1 | 1.0 | >8000 |
| 0.5 | 0.3 | 3.0 | 7000 |
| 0.5 | 0.3 | 10.0 | >8000 |
| 0.5 | 3.5 | 3.5 | 6500 |
| 0.5 | 5.0 | 5.0 | 7500 |

TABLE 4-continued

| $Fe_3O_4$ (mg/ml) | DPPA (mg/ml) | Synperonic F108 (mg/ml) | AUC (% min) |
|---|---|---|---|
| 0.5 | 10.0 | 10.0 | 8000 |
| 0.5 | 0.1 | 10.0 | ≈4000 |
| 0.5 | 1.0 | 10.0 | 6500 | experiments have also shown that particles produced under the same conditions but with a much lower amount of surfactant exhibited equally poor protection from premature removal. The rationale behind these results indicates that too much surfactant may disperse the phospholipid or the monoester so much that the affinity for the magnetite particle is destroyed and, with it, appropriate conditions for the formation of the urchin-like structure. By the same token, particles prepared with too little surfactant agglomerate are not protected from fast removal from blood.

We claim:

1. A method of making a particle for use in the NMR blood-pool imaging of human or animal patients, said particle comprising a magnetite iron oxide core and a layer of at least one amphipatic compound having a negatively charged phosphorus containing head moiety bonded to a hydrophobic tail moiety and one or more surfactants, said method comprising the steps of:

(a) selecting said amphipatic compound from an alkyl, alkenyl or cycloalkyl mono ester of phosphoric acid or a phospholipid in a micellar form;

(b) selecting at least one of said surfactants from physiologically acceptable non-ionic surfactants;

(c) suspending in an aqueous phase: (i) magnetite iron oxide particles, (ii) at least one of the selected amphipatic compounds and (iii) at least one of the selected non-ionic surfactants to form a mixture; and (d) energizing the mixture by sonicating, microfluidizing or heating to organize the molecules of the amphipatic compound relative to the iron oxide core so that the phosphorus containing head moiety of the amphipatic compound is pointing towards the iron oxide core and the hydrophobic tail moiety protrudes therefrom, the negatively charged head moiety having the negative charges of two oxygen atoms available for interaction with the core and the hydrophobic tail moiety having at least eight carbon atoms, thereby producing three dimensional structures around said iron oxide particles.

2. A method of making a particle for use in the NMR blood-pool imaging of human or animal patients, said particle comprising a magnetite iron oxide core and a layer of at least one amphipatic compound having a negatively charged phosphorus containing head moiety bonded to a hydrophobic tail moiety and one or more surfactants, said method comprising the steps of:

(a) selecting said amphipatic compound from an alkyl, alkenyl or cycloalkyl mono ester of phosphoric acid or a phospholipid in a micellar form;

(b) selecting at least one of said surfactants from physiologically acceptable non-ionic surfactants;

(c) suspending in an aqueous phase: (i) magnetite iron oxide particles, and (ii) at least one of the selected amphipatic compounds to form a mixture;

(d) energizing the mixture by sonicating, microfluidizing or heating to organize the molecules of the amphipatic compound relative to the iron oxide core so that the phosphorus containing head moiety of the amphipatic compound is pointing towards the iron oxide core and the hydrophobic tail moiety protrudes therefrom, the negatively charged head moiety having the negative charges of two oxygen atoms available for interaction with the core and the hydrophobic tail moiety having at least eight carbon atoms, thereby producing three dimensional structures around said iron oxide particles;

(e) adding said non-ionic surfactant to the mixture of the iron oxide and the amphipatic compound; and (f) optionally repeating the energizing step.

3. The method of claim 1 including the additional step of sterilizing or lyophilizing or both.

4. The method of claim 1 or 2, wherein the non-ionic surfactant consists of at least one block copolymer having polyoxyethylene and polyoxpropylene segments or polyethyleneglycol alkylether.

5. The method of claim 1 or 2, wherein the non-ionic surfactant is intertwined with the amphipatic compound.

6. The method of claim 1 or 2 wherein the alkyl or alkenyl group of the amphipatic compound contains at least ten carbon atoms.

7. The method of claim 1 or 2, wherein the phospholipid in micellar form consists of an organic mono-phosphate ester of a substituted or partially substituted polyalcohol, at least one functional group of said polyalcohol being esterified by a saturated or unsaturated, aliphatic fatty acid, or etherified by a saturated or unsaturated alcohol, the other two acidic functions of the phosphoric add being either free or salified with alkali or earth alkali metals.

8. The method of claim 7, wherein the phospholipid is a monophosphate of a fatty acid glyceride selected from the group consisting of dimyristoylphosphatidic acid, dipalmitolphosphatidic acid and distearoylphosphatidic acid.

* * * * *